(12) United States Patent
Porzel et al.

(10) Patent No.: US 9,421,018 B2
(45) Date of Patent: Aug. 23, 2016

(54) METHODS OF DESIGNING MOLDS FOR MACHINING COST REDUCTION

(71) Applicant: Smith & Nephew, Inc., Memphis, TN (US)

(72) Inventors: Alec Paul Porzel, Collierville, TN (US); Robert H Dyer, Bartlett, TN (US); Thomas William Lux, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/359,621

(22) PCT Filed: Nov. 20, 2012

(86) PCT No.: PCT/US2012/066068
§ 371 (c)(1),
(2) Date: May 21, 2014

(87) PCT Pub. No.: WO2013/078206
PCT Pub. Date: May 30, 2013

(65) Prior Publication Data
US 2014/0343558 A1  Nov. 20, 2014

Related U.S. Application Data

(60) Provisional application No. 61/562,006, filed on Nov. 21, 2011.

(51) Int. Cl.
A61B 17/15 (2006.01)
B22F 3/24 (2006.01)
(Continued)

(52) U.S. Cl.
CPC ............ A61B 17/154 (2013.01); B22F 3/225 (2013.01); B22F 3/24 (2013.01); B22F 5/10 (2013.01);
(Continued)

(58) Field of Classification Search
CPC .......... B22F 3/225; B28B 3/24; C04B 35/64; A61B 2017/00526; A61B 17/154
USPC .................. 606/88, 87, 86 R, 96, 79, 89, 53; 419/26, 28, 44
See application file for complete search history.

(56) References Cited

U.S. PATENT DOCUMENTS 6,619,370 B2 * 9/2003 Sakamoto ............ B22D 17/007
164/113
2002/0131886 A1 9/2002 Kuhns
(Continued)

FOREIGN PATENT DOCUMENTS

CN 1913844 A 2/2007
WO 0023217 A1 4/2000
(Continued)

OTHER PUBLICATIONS

International Search Report; International Searching Authority; International Application No. PCT/US2012/066068; Feb. 12, 2013; 3 pages.
(Continued)

Primary Examiner — David Bates
(74) Attorney, Agent, or Firm — Taft Stettinius & Hollister LLP

(57) ABSTRACT

An orthopaedic knee cutting block prepared by a process comprising the steps of: creating a mold with a first core detail and a second core detail, each of the core details corresponding to a volume; filling the mold with a mixture of a binder and a metal; releasing a green part from the mold, the green part having a first void corresponding to the first core detail and a second void corresponding to the second core detail; removing the binder from the green part; heating the green part to create a sintered part; and machining the part by sawing a cutting slot such that the cutting slot overlaps with the first void and the second void. Alternatively, the orthopaedic knee cutting instrument may be made by a simple metal casting method.

17 Claims, 4 Drawing Sheets

(51) Int. Cl.
   *B22F 3/22* (2006.01)
   *B22F 5/10* (2006.01)
   *A61B 17/00* (2006.01)

(52) U.S. Cl.
   CPC ............ *A61B 17/155* (2013.01); *A61B 17/157* (2013.01); *A61B 2017/00526* (2013.01); *B22F 2003/245* (2013.01); *Y10T 29/4998* (2015.01)

(56) References Cited

U.S. PATENT DOCUMENTS

| | | | | |
|---|---|---|---|---|
| 2007/0073305 | A1* | 3/2007 | Lionberger et al. | 606/87 |
| 2007/0282347 | A9* | 12/2007 | Grimm et al. | 606/96 |
| 2008/0295312 | A1 | 12/2008 | Molz et al. | |
| 2010/0168752 | A1* | 7/2010 | Edwards | A61B 17/155 606/87 |
| 2010/0262149 | A1* | 10/2010 | Charles et al. | 606/87 |
| 2011/0010904 | A1* | 1/2011 | Liufu et al. | 29/25.35 |
| 2011/0046629 | A1* | 2/2011 | Green, II | A61B 17/155 606/88 |
| 2011/0082494 | A1* | 4/2011 | Kerr et al. | 606/205 |
| 2011/0238073 | A1* | 9/2011 | Lang et al. | 606/89 |

FOREIGN PATENT DOCUMENTS

| | | |
|---|---|---|
| WO | 0114602 A2 | 3/2001 |
| WO | 2007097853 A2 | 8/2007 |
| WO | 2010112588 A1 | 10/2010 |
| WO | 2010124398 A1 | 11/2010 |

OTHER PUBLICATIONS

European Examination Report; European Patent Office; European Application No. 12852348.7; Aug. 5, 2015; 6 pages.
Chinese Search Report; Chinese Patent Office; Chinese Patent Application No. 201280057351.5; Jan. 26, 2016; 6 pages.
Chinese First Office Action; Chinese Patent Office; Chinese Patent Application No. 201280057351.5; Feb. 3, 2016; 23 pages.

* cited by examiner

FIG. 1
PRIOR ART
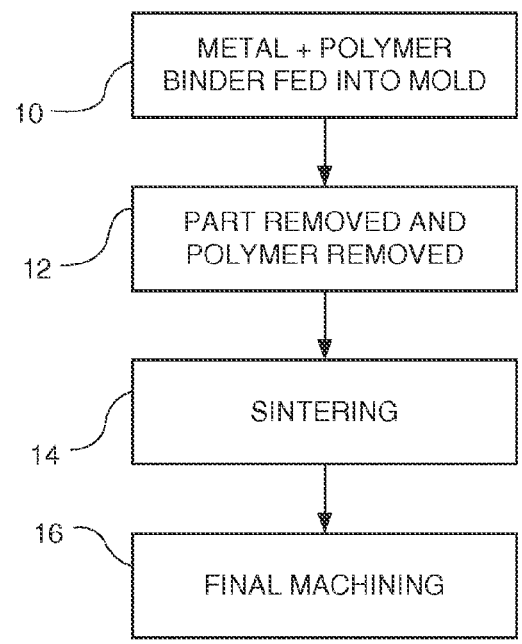
- 10 — METAL + POLYMER BINDER FED INTO MOLD
- 12 — PART REMOVED AND POLYMER REMOVED
- 14 — SINTERING
- 16 — FINAL MACHINING
FIG. 2
PRIOR ART
FIG. 3
PRIOR ART
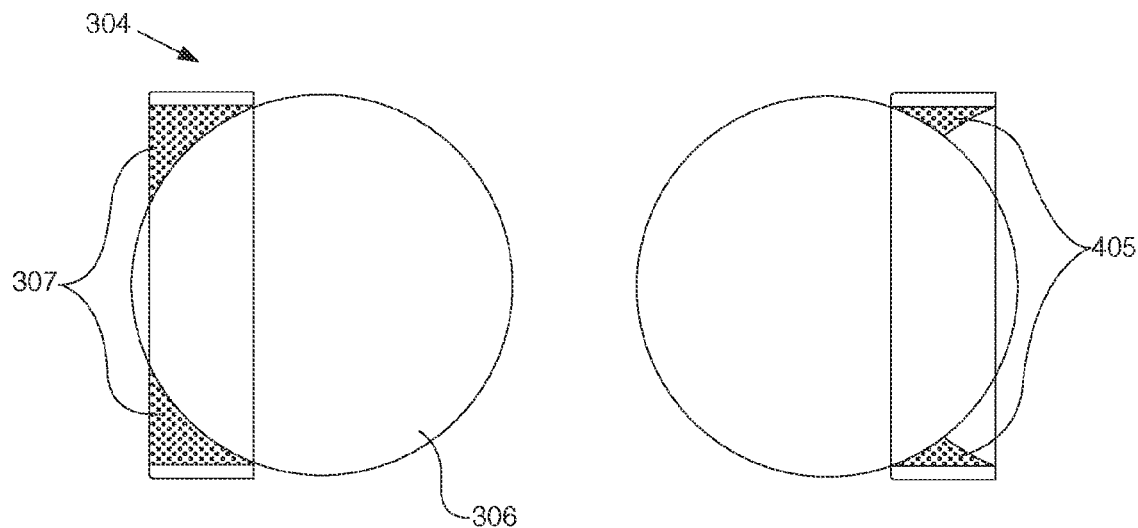

US 9,421,018 B2

METHODS OF DESIGNING MOLDS FOR MACHINING COST REDUCTION

CROSS-REFERENCE TO RELATED APPLICATIONS

This application is a United States National Phase filing of International Application No. PCT/US2012/066068 filed on Nov. 20, 2012, which claims the benefit of U.S. Provisional Application No. 61/562,006, filed Nov. 21, 2011. The disclosure of each prior application is incorporated by reference in its entirety.

BACKGROUND OF THE INVENTION

The present invention relates generally to methods of designing molds. More specifically, the invention relates to methods of designing molds for orthopedic instruments and implants.

The traditional approaches to creating a shaped metal object include the lost wax and sand casting methods. Both casting methods rely on creating a mold of the object, either with a sand cavity or with a wax mold, then pouring in a liquefied metal. The metal fills the mold cavity and cools. Once the metal solidifies, the mold can be broken and the part removed. Alternatively, metal objects can be machined into shapes from a billet. For cast parts, secondary machining is usually necessary to meet tolerances and/or to achieve surface finishes and the like. However, machining operations require material removal and can be inefficient and costly.

Metal injection molding (MIM) allows net-shape or near net-shape metal components to be made in high volumes without expensive machining costs. Referring to FIG. 1, the MIM process starts in step 10 with mixing a metal powder and a polymeric binder to create a material that can be injected into a mold cavity. The binder provides the mixture with the appropriate rheological properties for handling, molding and later ease of removal from the die. The mixture is then heated in an injection mold barrel to an appropriate consistency and injected into a mold cavity to take the shape of the mold. The injection molding machines can be the same ones as used for plastic injection molded parts. Once the mold has been formed, the green part is ejected from the mold in step 12. The binder is then removed from the green part, typically by introducing the part to a solvent or by burning out the polymer. The next step 14 is sintering the part in an oven to partially melt the metal particles. Temperatures typically reach about 1000 degrees Celsius during sintering. During this stage, the part may shrink 15-20 percent as the metal particles consolidate. After sintering, the part has a density very close to that of a traditionally formed part. Finally, in step 16, the sintered part is machined to its final shape.

One embodiment of the final machining steps of the prior art is shown in FIGS. 2 and 3. FIG. 2 illustrates a schematic partial sectional view of a cutting block 304 with slitting saw blade 306 inserted to its maximum depth Slitting saw blades may enter the face of cutting block 304 to form a precisely sized slot for the surgical saw blade. However, as can be seen in FIG. 2, the curvature of the blades results in incomplete removal of the metal in the slot, illustrated at 307. In an attempt to clean up the slot, blade 306 may be inserted from the other side of cutting block 304. This second machining step is illustrated in FIG. 3. As can be seem, a "dragon's tooth" 405 is still present that must be removed by another operation. Other operations include using a wire EDM to finish the part, filing the part, milling, etc. These operations all add extra cost and time to the final product.

Among the advantages of metal injection molding are the greater design flexibility and lower machining costs. Whereas traditional machining methods rely on the removal of material from a part, MIM parts can be built to near net shape and later machining costs can be lowered or eliminated. All the benefits and design constraints of plastic metal injection molding essentially carry over to MIM.

Depending on the tolerances required for the final part, further machining may be necessary. In general, larger objects produced with MIM need much more subsequent machining than smaller parts, limiting MIM's applicability to smaller objects. For example, a typical tolerance for an unfinished MIM'ed part is $\pm 5/1000"$ per inch, but a cutting slot tolerance for an orthopedic cutting block may be $\pm 1/1000"$ per inch, so the finished MIM part must sometimes be machined to meet tolerances. Similar tolerances may be needed for implant components such as femoral stems, tibial baseplates, knee arthroplasty femoral components and other orthopedic implants.

Although MIM is becoming widely used, many products still need additional machining operations due to an inability to meet the fine tolerances needed for some applications. This is especially true for orthopedic cutting blocks and implants. Therefore, there is a continuing need to improve the design of molds used in a MIM or casting process.

SUMMARY OF THE INVENTION

The various embodiments of the present invention described below and shown in the Figures describe methods of mold design that increase the efficiency of later machining operations.

One aspect of the disclosure discloses an orthopaedic knee cutting block prepared by a process comprising the steps of: creating a mold with a first core detail and a second core detail, each of the core details corresponding to a volume; filling the mold with a mixture of a binder and a metal; releasing a green part from the mold, the green part having a first void corresponding to the first core detail and a second void corresponding to the second core detail; removing the binder from the green part; heating the green part to create a sintered part; and machining the sintered part by sawing a cutting slot such that the cutting slot overlaps with the first void and the second void.

In some embodiments, the first and second core details are located on a proximal portion.

In some embodiments, the cutting slot is an anterior cutting slot.

In some embodiments, the orthopaedic knee cutting block may include a posterior cutting slot.

In some embodiments, the orthopaedic knee cutting block may include at least one chamfer cut slot.

In some embodiments, the orthopaedic knee cutting block may include a countersink.

One aspect of the disclosure discloses a method of designing a mold for an orthopedic instrument or implant, comprising creating a mold with core details corresponding to a volume that a single machining operation cannot remove; filling the mold with a mixture of a binder and a metal; releasing a green part from the mold; removing the binder from the green part; heating the green part to create a sintered part; and machining the sintered part.

Another aspect of the disclosure discloses a method of designing a mold for an orthopedic instrument or implant, comprising creating a mold with core details corresponding to a volume that simplifies a later machining operation; filling the mold with a mixture of a binder and a metal; releasing a green part from the mold; removing the binder from the green part; heating the green part to create a sintered part; and machining the sintered part.

Still further aspects of the disclosure include a method of designing a mold for an orthopedic instrument or implant, comprising creating a mold with core details corresponding to a volume that a single machining operation will not be able to remove; filling the mold with a molten metal; allowing the molten metal to solidify; releasing a part from the mold; and machining the part.

Yet further aspects of the disclosure include a method of designing a mold for an orthopedic instrument or implant, comprising creating a mold with core details corresponding to a volume that simplifies a later machining operation; filling the mold with a molten metal; allowing the molten metal to solidify; releasing a part from the mold; and machining the part.

Other aspects of the disclosure include wherein the orthopedic instrument is a cutting block. Still further aspects include wherein the machining operation uses a slitting saw on a milling machine and wherein the volume is tooth-shaped or torus-shaped.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings illustrate the embodiments of the invention and together with the written description serve to explain the principles, characteristics, and features of the invention. In the drawings:

FIG. 1 is a block diagram of a metal-injection-molding (MIM) process.

FIG. 2 shows a schematic partial sectional view of a prior art unfinished cutting block being machined.

FIG. 3 a schematic partial sectional view of a prior art unfinished cutting block being machined subsequent to the step shown in FIG. 2.

DETAILED DESCRIPTION OF THE EMBODIMENTS

The following description of the depicted embodiment(s) is merely exemplary in nature and is in no way intended to limit the invention, its application, or uses.

Embodiments of the present disclosure provide orthopedic cutting blocks and methods of manufacture that reduce secondary machining operations and/or make machining operations easier to perform.

"Core details" refers to the features on the inside of a mold that defines the shape of the space within a mold and the external surface of an object produced in the mold. These features can take any three-dimensional shape.

Figure 4:
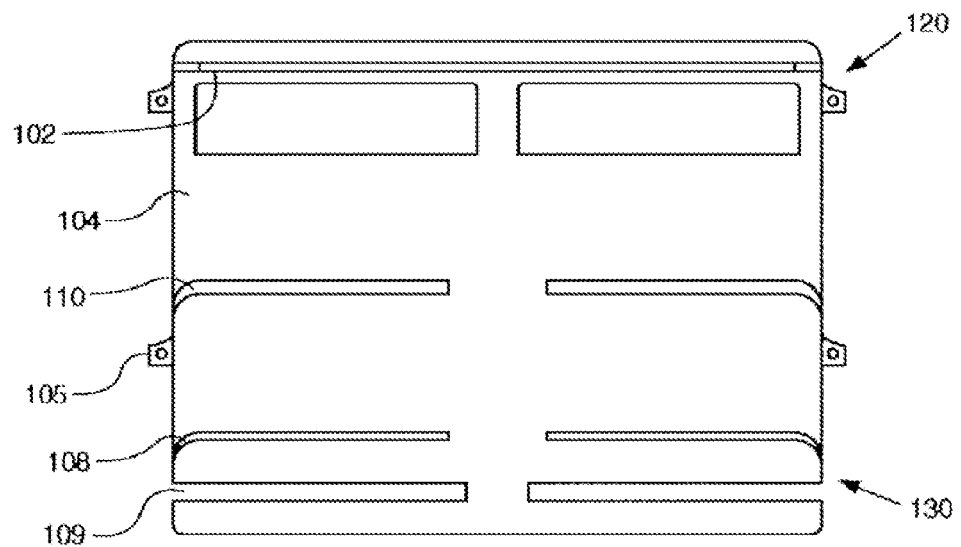
FIG. 4 shows a front view of a finished orthopedic cutting block.

FIG. 4 illustrates a finished cutting block 104. The cutting block 104 has a proximal portion 120 and a distal portion 130. The cutting block includes a captive 102, or close-ended cutting slot. In use, the cutting block 104 is typically connected to a patient's bone using pins that are inserted into holes 105. After the cutting block is placed on the patient's bone, a surgical saw blade is inserted into the captive 102 and is used to make a cut in the patient's bone. The cutting block 104 may include other cutting slots, such as slots 108, 109, and 110. One of ordinary skill in the art would understand that these cutting slots 102, 108, 109, 110 must be placed at the right locations and orientations to ensure the bone cuts are made in the desired locations. Cutting blocks like the one shown in FIG. 4 have traditionally been made from a piece of bar stock that is subsequently machined into shape. In current designs, the edges of captive 102 as shown in FIG. 4 may have been formed by a wire electrical discharge machine ("EDM") or by a slitting saw blade or other milling operation.

Figure 5:
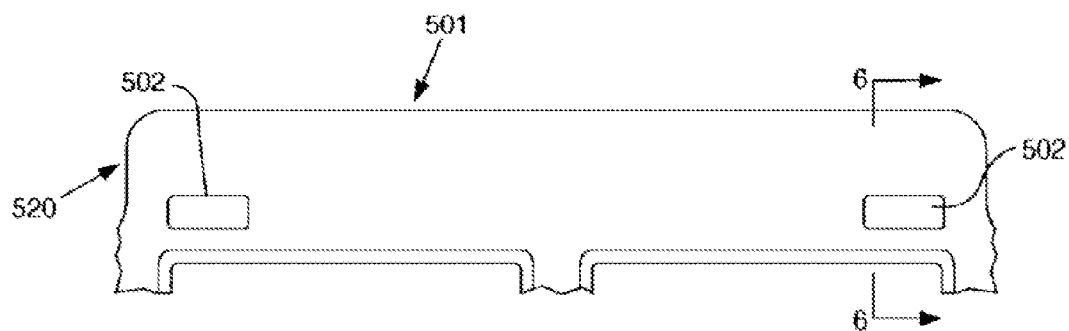
FIG. 5 shows a partial view of an unfinished orthopedic cutting block.
Figure 6:
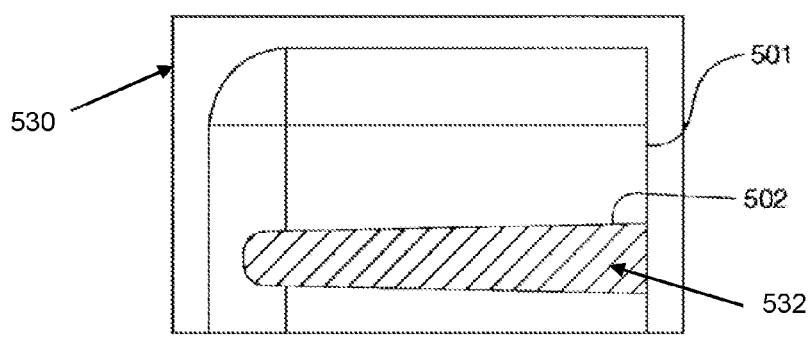
FIG. 6 shows a side view of a cutting block with a cavity detail.
Figure 9:
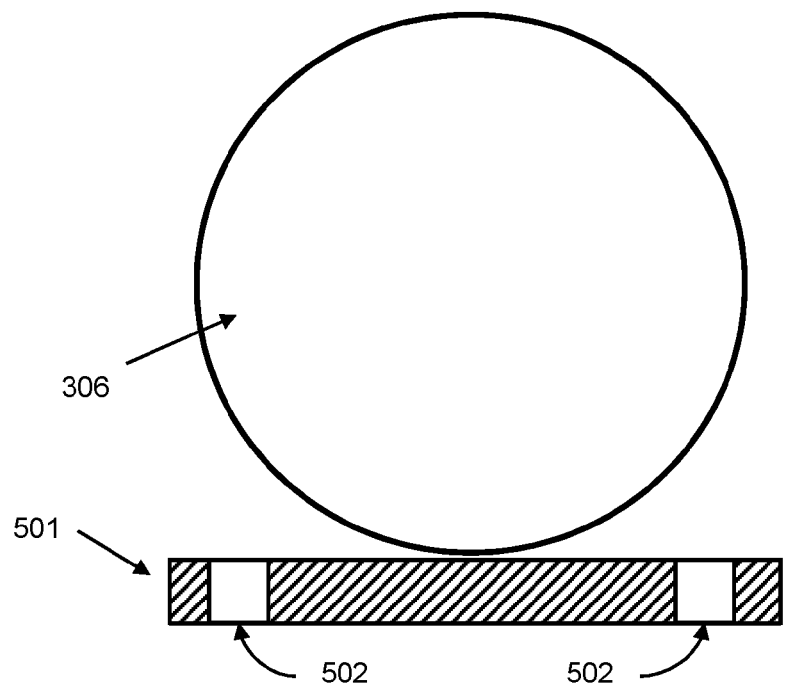
FIGS. 9 and 10 show a schematic partial sectional view of the unfinished orthopedic cutting block illustrated in FIG. 5 being machined to the finished orthopedic cutting block illustrated in FIG. 7.
Figure 10:
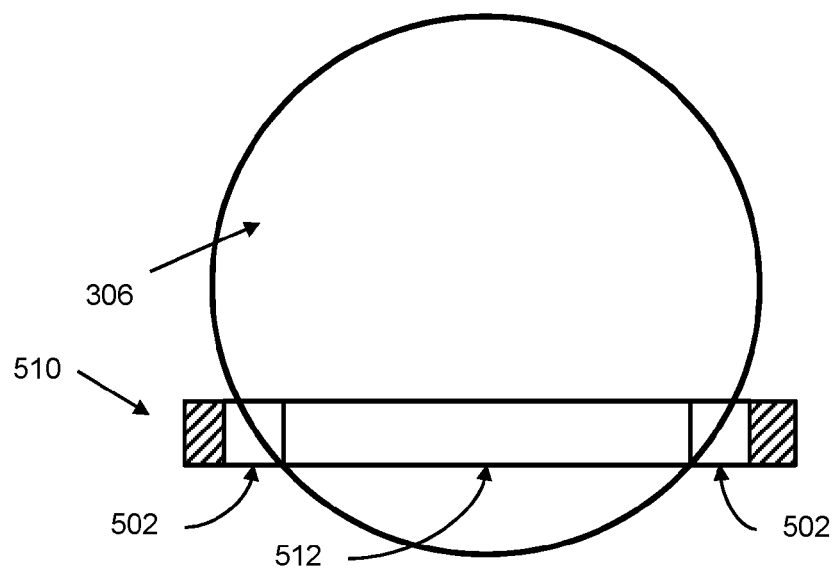

FIG. 5 illustrates one embodiment of the invention. FIG. 5 is a frontal view of an unfinished orthopedic cutting block 501, such as a "green" part or "as cast" part. The unfinished block is shown just before machining. The orthopaedic cutting block 501 may include one or more voids 502 in a proximal portion 520. The voids 502 also may be called cavities in the cutting block 501. The void 502 is present because of a corresponding volume in a core detail 532 in the material mold 530 (FIG. 6). The cutting block mold 530 is designed so that the free space occupied by void 502 corresponds to the volume that cannot be removed by a single slitting saw operation (FIGS. 9 and 10). Therefore, the final machining operation is quicker and cheaper because the part only needs to be plunged with a slitting saw 306 and does not need any other machining operations, such as wire EDM. One of ordinary skill in the art can readily envision incorporating these types of core details 532 into other types of fabrication methods, such as sand casting, lost wax casting, or selective laser sintering.

FIG. 6 illustrates a partial sectional side view of the void 502 and the corresponding core detail 532. The sides of the void 502 may be tapered for mold release.

Figure 7:
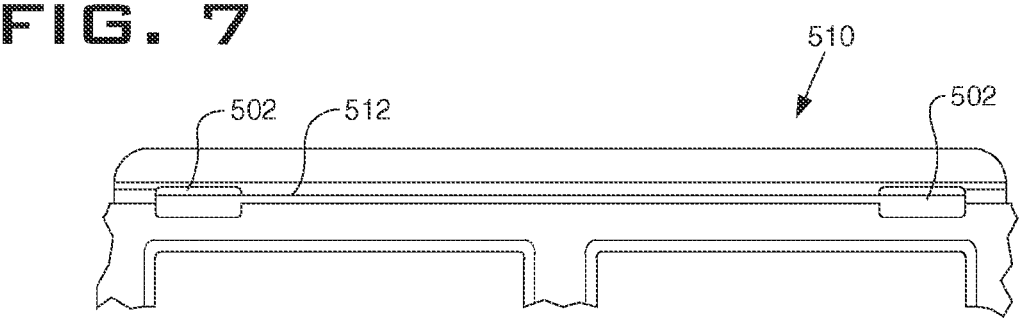
FIG. 7 shows a partial view of a finished orthopaedic cutting block.

FIG. 7 is a frontal view of a finished orthopedic cutting block 510 with a machined slot 512. The machined slot 512 overlaps or engages the voids 502.

Figure 8:
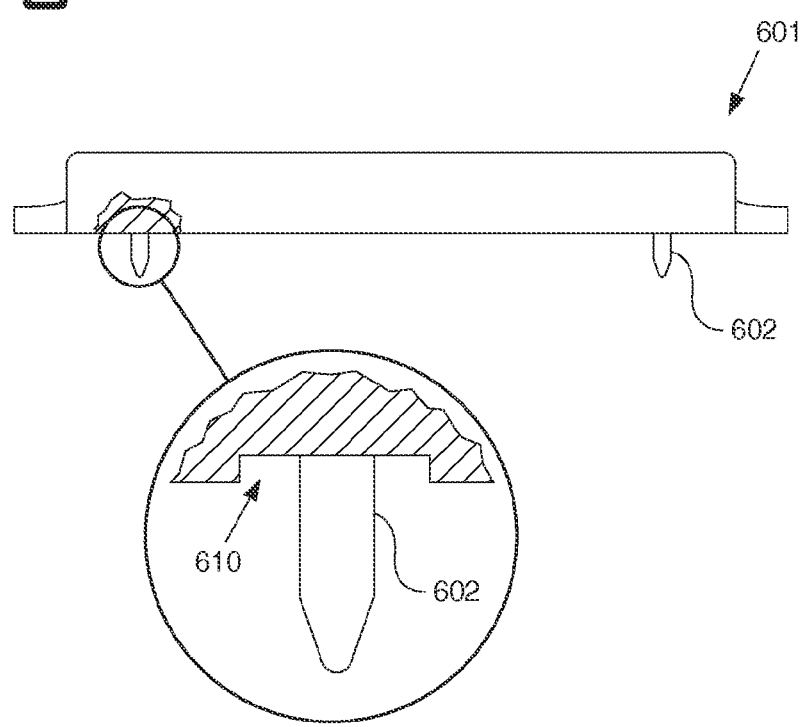
FIG. 8 shows a detailed view of a countersink around a spike.

Another embodiment of the present disclosure is shown in FIG. 8, an end-view of cutting block 601. Cutting block 601 may have one or more spikes 602 that are used to secure the cutting block to the bone. It is advantageous to provide a countersink 610 at the base of the spikes. Alternatively, the countersink 610 may be called an undercut area. The countersink can be incorporated in the mold as a core detail. Because the primary datum on the cutting block is created during the machining of the near net shape MIM body, the countersink allows for reduced machining time, as the full geometry of the metal spike can be created during the molding process, and creation of the primary datum (through milling or grinding) can be done without having to "walk" around the metal spikes while avoiding the challenge of "matching" surfaces. If the countersink were not present the mill bit could nick the metal bone spike and create a mismatched surface. Instead of trying to mill right up against the spikes in order to create the primary datum surface, the tool can maintain clearance and create the full datum surface with no risk of contacting the spikes. In the depicted embodiment, the countersink 610 is shown as a circular depression but other shapes may be used. As examples, the countersink 610 may be square, rectangular, triangular, or elliptical.

The design methods of the present disclosure may be applied to any situation where a MIM part needs post-machining. In general, it may be said that it is more applicable to larger parts, where the inherent tolerances of MIM design become limiting.

The orthopaedic knee cutting block instrument can be manufactured in several different ways. As a first example, the orthopaedic knee cutting block can be prepared by a process having the steps of: creating a mold with a first core detail and a second core detail, each of the core details corresponding to a volume; filling the mold with a mixture of a binder and a metal; releasing a green part from the mold, the green part having a first void corresponding to the first core detail and a second void corresponding to the second core detail; removing the binder from the green part; heating the green part to create a sintered part; and machining the sintered part by sawing a cutting slot such that the cutting slot overlaps with the first void and the second void. As a second example, the orthopedic knee cutting block instrument is manufactured by: creating a mold with a core detail corresponding to a volume; filling the mold with a molten metal; allowing the molten metal to solidify to produce a part; releasing the part from the mold, the part having a void corresponding to the core detail; and machining a slot in the part, wherein the slot intersects the void.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the invention should not be limited by any of the above-described exemplary embodiments, but should be defined only in accordance with the claims and their equivalents.

What is claimed is:

1. A method of preparing an orthopaedic knee cutting block, the method comprising the steps of:
   a. creating a mold with a first core detail and a second core detail, each of the core details corresponding to a volume;
   b. filling the mold with a mixture of a binder and a metal;
   c. releasing a green part from the mold, the green part having a first void corresponding to the first core detail and a second void corresponding to the second core detail;
   d. removing the binder from the green part;
   e. heating the green part to create a sintered part, the sintered part including a region between the first void and the second void, the region including a first section of material and a second section of material; and
   f. plunging a slitting saw into the sintered part to remove the first section of material from the region between the first void and the second void, thereby forming a cutting slot which overlaps with the first void and the second void;
   wherein the orthopaedic knee cutting block includes the second section of material in the region between the first void and the second void.

2. The method of claim 1, wherein the first and second core details are located on a proximal portion.

3. The method of claim 1, wherein the cutting slot is an anterior cutting slot.

4. The method of claim 1, wherein the orthopaedic knee cutting block further comprises a posterior cutting slot.

5. The method of claim 1, wherein the orthopaedic knee cutting block further comprises at least one chamfer cut slot.

6. The method of claim 1, wherein the orthopaedic knee cutting block further comprises a spike and a countersink formed at the base of the spike.

7. The method of claim 1, wherein the volumes corresponding to the first and second core details correspond to volumes of the sintered part that cannot be removed by plunging the slitting saw to form the cutting slot.

8. The method of claim 7, wherein the cutting block comprises a captive including the first void, the second void, the cutting slot, and the volumes of the sintered part that cannot be removed by plunging the slitting saw to form the cutting slot.

9. The method of claim 1, wherein the first void, the second void, and the cutting slot define a captive including a first edge defined by a wall of the first void and a second edge defined by a wall of the second void.

10. A method of manufacturing an orthopedic knee cutting block instrument comprising:
    a. creating a mold with a core detail;
    b. filling the mold with a mixture of a binder and a metal;
    c. releasing a green part from the mold, the green part having a void created by the core detail;
    d. removing the binder from the green part;
    e. heating the green part to create a sintered part; and
    f. plunging a slitting saw to form a slot in the sintered part, wherein the slot intersects the void;
    wherein the void created by the core detail corresponds to a volume which is aligned with the slot and cannot be removed from the sintered part by the plunging.

11. The method of claim 10, wherein the core detail is located on a proximal portion.

12. The method of claim 10, wherein the slot is an anterior cutting slot.

13. The method of claim 10, wherein the creating further includes creating the mold with a second core detail, wherein the green part has a second void created by the second core detail, wherein the slot further intersects the second void, and wherein a captive is defined by the void, the second void, and the slot.

14. A method of manufacturing an orthopedic knee cutting block instrument comprising:
    a. creating a mold with a core detail corresponding to a volume;
    b. filling the mold with a molten metal;
    c. allowing the molten metal to solidify to produce a part;
    d. releasing the part from the mold, the part having a void corresponding to the core detail; and
    e. plunging a slitting saw to form a slot in the part, wherein the slot intersects the void.

15. The method of claim 14, wherein the core detail is located on a proximal portion.

16. The method of claim 14, wherein the slot is an anterior cutting slot.

17. The method of claim 13, wherein the captive is formed solely by plunging the slitting saw such that the slot intersects the void and the second void.

* * * * *